United States Patent [19]

Connor

[11] 4,210,758
[45] Jul. 1, 1980

[54] 1,5-DIHYDRO-1,5-DIOXO-N-1H-TETRAZOL-5-YL-4H-[1]BENZOPYRANO[3,4-B]PYRIDINE-2-CARBOXAMIDES

[75] Inventor: David T. Connor, Ann Arbor, Mich.

[73] Assignee: Warner-Lambert Company, Morris Plains, N.J.

[21] Appl. No.: 22,391

[22] Filed: Mar. 21, 1979

[51] Int. Cl.² .......................................... C07D 491/04
[52] U.S. Cl. .................................... 546/92; 424/256; 260/343.45
[58] Field of Search .......................................... 546/92

[56] References Cited

U.S. PATENT DOCUMENTS 3,689,497  9/1972  Brown et al. ................... 546/92 OR

*Primary Examiner*—John D. Randolph
*Attorney, Agent, or Firm*—Stephen Raines; Albert H. Graddis; Frank S. Chow

[57] ABSTRACT

The present invention relates to 1,5-dihydro-1,5-dioxo-N-1H-tetrazol-5-yl-4H-[1]benzopyrano[3,4-b]pyridine-2-carboxamides having the following structural formula:

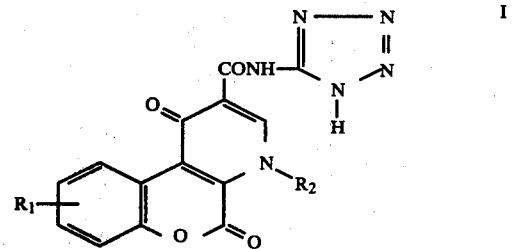

wherein $R_1$ is hydrogen, halogen, hydroxy, lower alkoxy, lower alkyl, or nitro and $R_2$ is hydrogen or lower alkyl and the pharmaceutically acceptable salts thereof.

These compounds and their pharmaceutically acceptable salts are useful in the management of allergic manifestations such as bronchial asthma, hay fever and the like.

7 Claims, No Drawings

1,5-DIHYDRO-1,5-DIOXO-N-1H-TETRAZOL-5-YL-4H-[1]BENZOPYRANO[3,4-B]PYRIDINE-2-CARBOXAMIDES

The present invention relates to certain benzopyrano derivatives and more particularly to 1,5-dihydro-1,5-dioxo-N-1H-tetrazol-5-yl-4H-[1]benzopyrano[3,4-b]pyridine-2-carboxamides having the following structural formula:

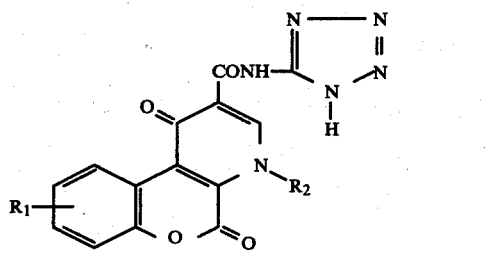

wherein $R_1$ is hydrogen, halogen, hydroxy, lower alkoxy, lower alkyl, or nitro and $R_2$ is hydrogen or lower alkyl and the pharmaceutically acceptable salts thereof.

In the above definitions for $R_1$ and $R_2$, the term "lower alkyl" and the lower alkyl portion of "lower alkoxy" is meant to include both straight and branched chain alkyl radicals having 1 to 6 carbon atoms, for example methyl, ethyl, propyl, isopropyl, n-butyl, and the like. The term "halogen" is meant to embrace all its four members i.e. iodine, bromine, fluorine, and chlorine.

The compounds of this invention, as well as their pharmaceutically acceptable salts, are active in the prevention of allergic reactions in mammals such as mice, rats and guinea pigs. Typically, using rats as the host, and employing the passive cutaneous anaphalaxis (PCA) test, which is described in *Life Sciences*, 7; 465 (1963), *Proc. Soc. Exptl. Biol. Med.*, 81; 585 (1952) and U.S. Pat. No. 4,076,720, the compounds of this invention or their salts were effective in preventing allergic manifestations at a dose level of 0.5 mg/kg to 100 mg/kg. Typically, the compound 1,5-dihydro-1,5-dioxo-N-1H-tetrazol-5-yl-4H-[1]benzopyrano[3,4-b]pyridine-2-carboxamide at an intraperitoneal dose of 5 mg/kg shows 100% inhibition of the allergic response and at an oral dose of 5 mg/kg 45% inhibition when tested in accordance with the aforedescribed test procedures.

The well known antiallergic compound cromolyn sodium shows 50% inhibition at 2 mg/kg intravenously in the PCA test.

The compounds in this invention including their salts are indicated in the management of mammals suffering from allergic manifestations such as bronchial asthma and hay fever. Generally speaking, a dose of 0.5 mg/kg to 100 mg/kg orally, parenterally, or by inhalation 1 to 3 times daily is suggested. As with any antiallergy therapy, the above dosage regiment must be titrated to individual needs by methods known to the healing arts.

According to a further feature of the present invention, there are provided pharmaceutical compositions which comprise as active ingredients, at least one of the compounds of this invention or their salts as hereinbefore defined, together with a pharmaceutical carrier. Thus for example, solid compositions for oral administration include compressed tablets, pills, dispensable powders and granules. In such solid compositions, the selective active ingredients are mixed with at least one inert diluent such as calcium carbonate, calcium sulphate, or lactose. These compositions may also comprise, as known to the pharmacist art additional substances other than diluents, such as lubricating agents for example magnesium stearate. The resulting dosage forms such as tablets are prepared by methods known to the pharmacist art.

Liquid compositions for oral administration include for example, solutions, suspensions, syrups and elixirs containing inert diluents commonly used in the preparation of such dosage forms for example, water and simple syrup.

Preparations for parenteral administration include for example, sterile aqueous or non-aqueous solutions or suspensions. Examples of non-aqueous solvents or suspending media are for example, propylglycol, vegetable oils such as olive oil and injectable organic esters such as ethyl oleate.

According to the present invention, compound I is prepared from $R_1$-substituted 3-aminocoumarin of the formula,

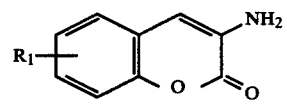

with diethyl ethoxymethylenemaloanate of the formula:

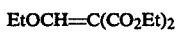

at a temperature of about 100° C. to 150° C. and typically at 120° C. over a period of two to six hours under an atmosphere of nitrogen to obtain a compound of the formula:

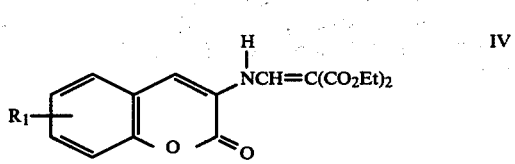

Heating compound IV, in diphenyl ether at elevated temperature such as from 274° C.–285° C. under an inert atmosphere such as under an atmosphere of nitrogen results in the production of a compound of the formula:

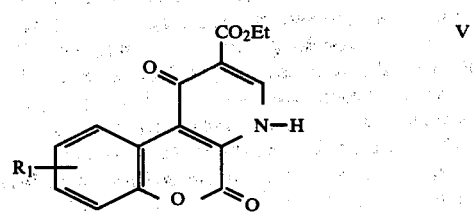

Treatment of Compound V with $R_2I$ results in the production of the compound of the formula:

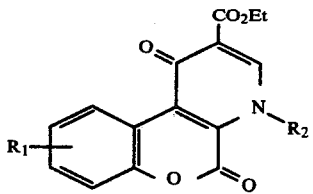

Hydrolysis of Compound VI yields a compound of the formula:

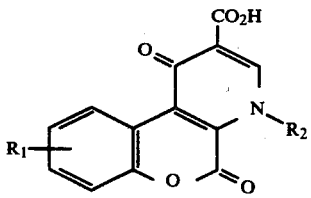

Finally, treatment of Compound VII with a compound of the formula:

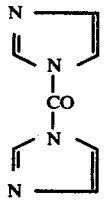

followed by treatment with a compound of the formula:

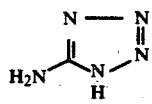

results in the production of the compounds of the present invention in which $R_2$ is lower alkyl.

To obtain those compounds in this invention in which $R_2$ is hydrogen, Compound V is hydrolized to obtain a compound of the structure:

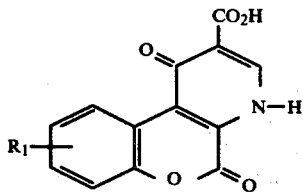

which is then in turn treated with 1,1-carbonyldiimidazole followed by treatment with Compound IX.

Generally speaking, the reaction between Compound IX with the imidazolides of VII or X is affected at elevated temperature such as 100° over a period of 60 minutes under an inert atmosphere such as nitrogen.

The starting $R_1$ substituted aminocoumarins are prepared in accordance with the method of F. W. Lynch, J. Chem. Soc., 101, 1758 (1912). This disclosure, as well as the disclosures in Life Sciences, Proc. Soc. Exptl. Biol. Med. and U.S. Pat. No. 4,076,720 referred to above, are incorporated herein by reference.

The $R_1$-substituted aminocoumarins may also be prepared by my disclosure in co-pending application Ser. No. 022,389 entitled (2-Oxo-2H-1-benzopyran-3-yl)aminooxacetic acids and their derivatives, filed concurrently herewith. This is also incorporated herein by reference.

The pharmaceutically acceptable salts of Compound I are prepared by treating compound I with an acid such as with a mineral acid, for example, hydrochloric, sulfuric, nitric and so on or an organic acid such as acetic using methods known in the art.

In order to further illustrate the practice in this invention, the following examples in which temperature referred to therein are in degrees centigrade are included:

EXAMPLE 1

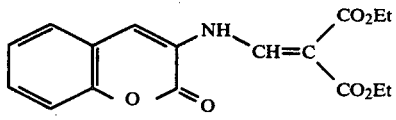

Diethyl{[(2-oxo-2H-1-benzopyran-3-yl)amino]methylene}malonate

A mixture of 3-aminocoumarin (30.0 g, 0.186 mole) and diethyl ethoxymethylenemalonate (75.0 g, 0.347 mole) is heated at 120° C. for 4 hours under nitrogen. The reaction mixture is cooled and triturated with hexane. The product is filtered off and washed with hexane. Recrystallization from ethyl acetate gives white crystals (55.0 g, 89%), mp. 134–135.

Anal. Calcd for $C_{17}H_{17}NO_6$: C, 61.63; H, 5.17; N, 4.23. Found: C, 61.44; H, 5.20; N, 4.14.

See also: M. A. Khan and A. L. Gemal, J. Heterocyclic Chemistry, 14, 1009 (1977).

EXAMPLE 2

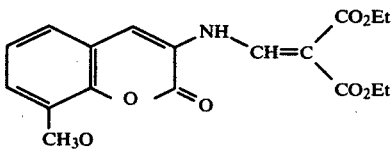

Diethyl{[(8-methoxy-2-oxo-2H-1-benzopyran-3-yl)amino]methylene}malonate

Prepared by the general method described for example 1 from 8-methoxy-3-aminocoumarin (3 g, 0.016 mole). Recrystallization from ethyl acetate gives yellow crystals (5.6 g, 99%), m.p. 193–194.

Anal. Calcd. for $C_{18}H_{19}NO_7$: C, 59.83; H, 5.30; N, 3.88. Found: C, 59.64; H, 5.34; N, 3.71.

EXAMPLE 3

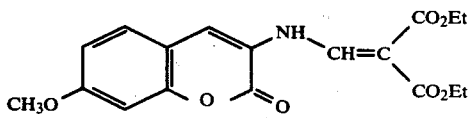

Diethyl{[(7-methoxy-2-oxo-2H-1-benzopyran-3-yl)amino]methylene}malonate

Prepared by the general method described for example 1 from 7-methoxy-3-aminocoumarin (8.0 g, 0.022 mole). Recrystallization from ethyl acetate gives yellow crystals (5.4 g, 36%), m.p. 202–203.

Anal. Calcd. for $C_{18}H_{19}NO_7$: C, 59.83; H, 5.30; N, 3.88. Found: C, 59.80; H, 5.67; N, 3.64.

EXAMPLE 4

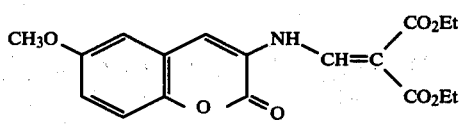

Diethyl{[(6-methoxy-2-oxo-2H-1-benzopyran-3-yl)amino]methlene}malonate

Prepared by the general method described for example 1 from 6-methoxy-3-aminocoumarin (18.0 g, 0.094 mole). Recrystallization from ethyl acetate gives yellow crystals (23 g, 68%), m.p. 134–136.

Anal. Calcd. for $C_{18}H_{19}NO_7$: C, 59.83; H, 5.30; N, 3.88. Found: C, 59.63; H, 5.50; N, 3.97.

EXAMPLE 5

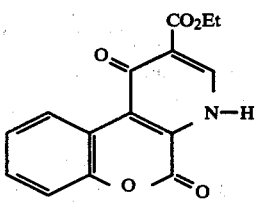

Ethyl 1,5-dihydro-1,5-dioxo-4H-1-benzopyrano[3,4-b]pyridine-2-carboxylate

A solution of diethyl{[(2-oxo-2H-1-benzopyran-2-yl)amino]methylene}-malonate (35.0 g) in diphenyl ether (300 ml) is heated at 275°–285° C. for 75 minutes under nitrogen. The reaction mixture is cooled and triturated with hexane. The brown solid is filtered off and washed with hexane. Recrystallization from dimethylformamide gives white crystals (30.0 g, 99%), m.p. 284–285.

Anal. Calcd. for $C_{15}H_{11}NO_5$: C, 63.15; H, 3.89; N, 4.91. Found: C, 63.17; H, 3.90; N, 5.06.

M. A. Khan and A. L. Gemal, *J. Heterocyclic Chem.*, 14, 1009 (1977).

EXAMPLE 6

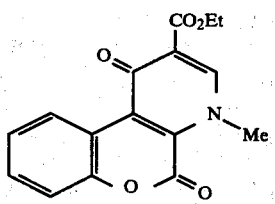

Ethyl 1,5-dihydro-1,5-dioxo-4-methyl-1-benzopyrano[3,4-b]pyridine-2-carboxylate A mixture of ethyl 1,5-dihydro-1,5-dioxo-4H-1-benzopyrano[3,4-b]-pyridine-2-carboxylate (11.0 g, 0.0386 mole), methyl iodide (22.0 g, 0.154 mole) and potassium carbonate (10.7 g, 0.077 mole) in dimethylformamide (175 ml) is heated at 80° C. for 3 hours under nitrogen. The reaction mixture is cooled and poured into excess cold water. The product, which precipitated, is filtered off and recrystallized from dimethylformamide as white crystals (7.2 g, 62%), m.p. 203°–208° C.

Anal. Calcd. for $C_{16}H_{13}NO_5$: C, 64.21; H, 4.38; N, 4.68. Found: C, 64.29; H, 4.45; N, 4.70.

EXAMPLE 7

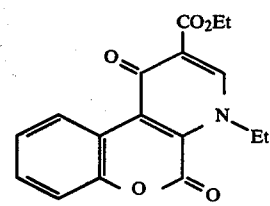

Ethyl 1,5-dihydro-1,5-dioxo-4-ethyl-1-benzopyrano[3,4-b]pyridine-2-carboxylate.

Prepared from ethyl 1,5-dihydro-1,5-dioxo-4H-1-benzopyrano[3,4-b]-pyridine-2-carboxylate (9.5 g, 0.033 mole) and ethyl iodide (20.8 g, 0.134 mole) by the method described for Ex. 6. Recrystallization from dimethylformamide gives white crystals (7.8 g, 75%), m.p. 180–181.

Anal. Calcd for $C_{17}H_{15}NO_5$: C, 65.17; H, 4.82; N, 4.47. Found: C, 65.03; H, 4.85; N, 4.44.

EXAMPLE 8

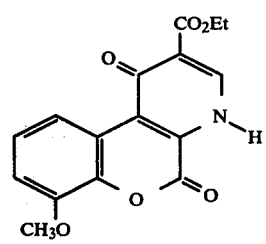

Ethyl 1,5-dihydro-1,5-dioxo-7-methoxy-4H-1-benzopyrano[3,4-b]pyridine-2-carboxylate.

Prepared by the general method described for example 5 from diethyl {[(8-methoxy-2-oxo-2H-1-benzopyran-3-yl)amino]methylene}malonate (10 g, 0.027 mole). Recrystallization from dimethylformamide gives yellow crystals (6.1 g, 70%), m.p. 264–265.

Anal. Calcd. for $C_{16}H_{13}NO_6 \cdot \frac{1}{2}Me_2NCHO$: C, 59.85; H, 4.67; N, 5.82. Found: C, 59.93; H, 4.58; N, 5.49.

EXAMPLE 9

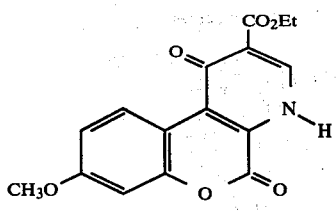

Ethyl 1,5-dihydro-1,5-dioxo-8-methoxy-4H-1-benzopyrano[3,4-b]pyridine-2-carboxylate Prepared by the general procedure described for example 5 from diethyl {[(7-methoxy-2-oxo-2H-1-benzopyran-3-yl)amino]methylene}-malonate (4.5 g, 0.0125 mole). Recrystallization from dimethylformamide gives yellow crystals (3.6 g, 84%), m.p. 295–296.

Anal. Calcd. for $C_{16}H_{13}NO_6$: C, 60.95; H, 4.16; N, 4.44. Found: C, 61.25; H, 4.18; N, 4.21.

EXAMPLE 10

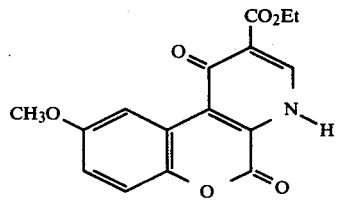

Ethyl 1,5-dihydro-1,5-dioxo-9-methoxy-4H-1-benzopyrano[3,4-b]pyridine-2-carboxylate Prepared by the general method described for example 5 from diethyl {[(6-methoxy-2-oxo-2H-1-benzopyran-3-yl)amino]methylene}malonate (16 g, 0.044 mole). Recrystallization from dimethylformamide gives pale yellow crystals (12 g, 90%), m.p. 253–254.

Anal. Calcd. for $C_{16}H_{13}NO_6$: C, 60.95; H, 4.16; N, 4.44. Found: C, 60.66; H, 4.16; N, 4.57.

EXAMPLE 11

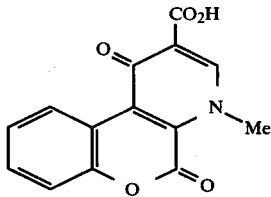

1,5-dihydro-1,5-dioxo-4-methyl-1-benzopyrano[3,4-b]pyridine-2-carboxylic acid A suspension of ethyl 1,5-dihydro-1,5-dioxo-4-methyl-1-benzopyrano[3,4-b]pyridine-2-carboxylate (4.5 g, 0.0158 mole) in 5 N hydrochloric acid (100 ml) is refluxed under nitrogen for 20 hours. The reaction mixture is cooled and diluted with water. The product is filtered off, washed with water and sucked dry. Recrystallization from dimethylformamide gives white crystals (3.5 g, 85%), m.p. 295–297 (dec.).

Anal. Calcd. for $C_{14}H_9NO_5$: C, 61.99; H, 3.34; N, 5.16. Found: C, 61.74; H, 3.45; N, 5.06.

EXAMPLE 12

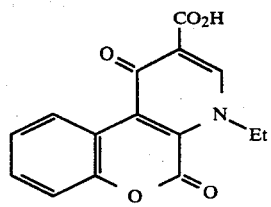

1,5-dihydro-1,5-dioxo-4-ethyl-1-benzopyrano[3,4-b]pyridine-2-carboxylic acid Prepared by the method described for Ex. 11 from ethyl 1,5-dihydro-1,5-dioxo-4-ethyl-1-benzopyrano[3,4-b]pyridine-2-carboxylate (2.9 g, 0.0093 mole). The product is washed with water, with acetone and sucked dry to give white crystals (2.61 g, 99%), m.p. 263–265.

Anal. Calcd. for $C_{15}H_{11}NO_5$: C, 63.16; H, 3.89; N, 4.91. Found: C, 63.31; H, 3.97; N, 5.16.

EXAMPLE 13

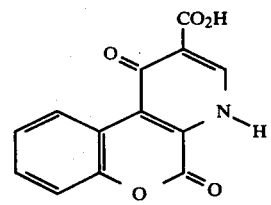

1,5-dihydro-1,5-dioxo-4H-1-benzopyrano[3,4-b]pyridine-2-carboxylic acid

Prepared by the method described for Ex. 11 from ethyl 1,5-dihydro-1,5-dioxo-4H-1-benzopyrano[3,4-b]pyridine-2-carboxylate (10 g, 0.035 mole). Recrystallization from dimethylformamide gives white crystals (5.32 g, 59%), m.p. 295–300 (dec.).

Anal. Calcd. for $C_{15}H_7NO_5$: C, 60.17; H, 2.74; N, 5.45. Found: C, 60.25; H, 2.79; N, 5.43.

EXAMPLE 14

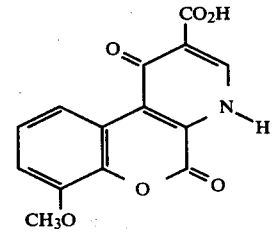

1,5-dihydro-1,5-dioxo-7-methoxy-4H-1-benzopyrano[3,4-b]pyridine-2-carboxylic acid Prepared by the general method described for example 11 from ethyl 1,5-dihydro-1,5-dioxo-7-methoxy-4H-1-benzopyrano[3,4-b]pyridine-2-carboxylate (3.38 g, 0.011 mole). Washing the product with water, with acetone and drying under vacuum gives white crystals (3.02 g, 97%), m.p. 330–335.

Anal. Calcd. for C₁₄H₉NO₆: C, 58.54; H, 3.16; N, 4.88. Found: C, 58.16; H, 3.19; N, 4.88.

EXAMPLE 15

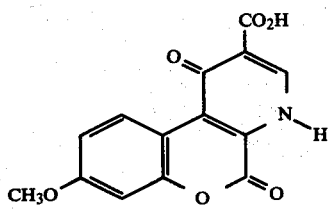

1,5-dihydro-1,5-dioxo-8-methoxy-4H-1-benzopyrano[3,4-b]pyridine-2-carboxylic acid Prepared by the general method described for example 11 from ethyl 1,5-dihydro-1,5-dioxo-8-methoxy-4H-1-benzopyrano[3,4-b]pyridine-2-carboxylate (2.50 g, 0.0087 mole). Washing the product with water, with acetone and drying under vacuum gives white crystals (2.15 g, 94%), m.p. 300–305.

Anal. Calcd. for C₁₄H₉NO₆.1/4H₂O: C, 57.63; H, 3.26; N, 4.80. Found: C, 57.35; H, 3.47; N, 4.64.

EXAMPLE 16

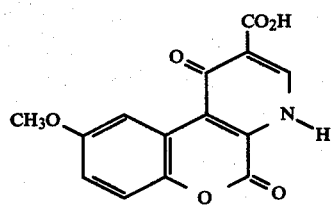

1,5-dihydro-1,5-dioxo-9-methoxy-4H-1-benzopyrano[3,4-b]pyridine-2-carboxylic acid Prepared by the general method described for example 11 from ethyl 1,5-dihydro-1,5-dioxo-9-methoxy-4H-1-benzopyrano[3,4-b]pyridine-2-carboxylate (14.0 g, 0.049 mole). Recrystallization from dimethylformamide gives white crystals (11.64 g, 90%), m.p. 320–325 (dec.).

Anal. Calcd. for C₁₄H₉NO₆: C, 58.54; H, 3.16; N, 4.88. Found: C, 58.36; H, 3.29; N, 4.82.

EXAMPLE 17

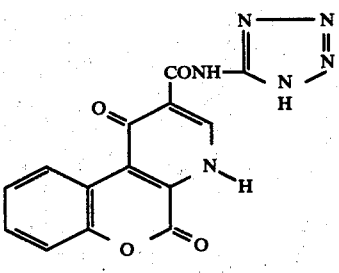

1,5-dihydro-1,5-dioxo-N-1H-tetrazol-5-yl-4H-[1]benzopyrano[3,4-b]pyridine-2-carboxamide A mixture of 1,5-dihydro-1,5-dioxo-4H-1-benzopyrano[3,4-b]pyridine-2-carboxylic acid (2.57 g, 0.01 mole) and 1,1'-carbonyldiimidazole (1.95 g, 0.012 mole) in dimethylformamide is heated at 100 for 60 minutes under nitrogen. The reaction mixture is cooled and stirred at room temperature for 15 minutes. 5-Aminotetrazole monohydrate (1.24 g, 0.012 mole) is added and the resulting mixture is heated at 100 for 60 minutes, cooled, and filtered. The product is recrystallized from dimethylformamide to give white crystals (1.1 g, 34%), m.p. above 300.

Anal. Calcd. for C₁₄H₈N₆O₄: C, 51.86; H, 2.49; N, 25.92. Found: C, 51.95; H, 2.91; N, 25.90.

EXAMPLE 18

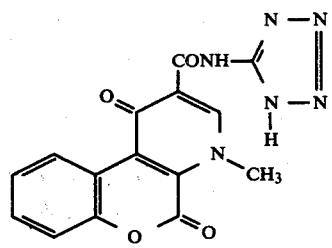

1,5-dihydro-4-methyl-1,5-dioxo-N-1H-tetrazol-5-yl-4H-[1]benzopyrano[3,4-b]pyridine-2-carboxamide Prepared by the method described for Ex. 17 from 1,5-dihydro-4-methyl-1,5-dioxo-4H-1-benzopyrano[3,4-b]pyridine-2-carboxylic acid (5.42 g, 0.02 mole), 1,1'-carbonyldiimidazole (6.48 g, 0.04 mole) and 5-aminotetrazole monohydrate (2.06 g, 0.02 mole) in dimethylformamide (90 ml). Recrystallization from dimethylformamide gives pale yellow crystals (6.4 g, 95%), m.p. above 300.

Anal. Calcd. for C₁₅H₁₀N₆O₄: C, 53.25; H, 2.98; N, 24.85. Found: C, 53.19; H, 3.24; N, 25.58.

EXAMPLE 19

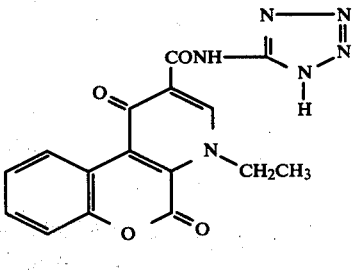

4-Ethyl-1,5-dihydro-1,5-dioxo-N-(1H-tetrazol-5-yl)-4H-[1]benzopyrano[3,4-b]pyridine-2-carboxamide Prepared by the method described for Ex. 17 from 4-ethyl-1,5-dihydro-1,5-dioxo-4H-1-benzopyrano[3,4-b]pyridine-2-carboxylic acid (2.2 g, 0.0077 mole), 1,1'-carbonyldiimidazole (2.4 g, 0.0148 mole) and 5-aminotetrazole monohydrate (0.76 g, 0.0076 mole) in dimethylformamide (30 ml). Recrystallization from dimethylformamide gives pale yellow crystals (1.5 g, 55%), m.p. above 300.

Anal. Calcd. for C₁₆H₁₂N₆O₄: C, 54.54; H, 3.43; N, 23.86. Found: C, 54.36; H, 3.53; N, 23.92.

EXAMPLE 20

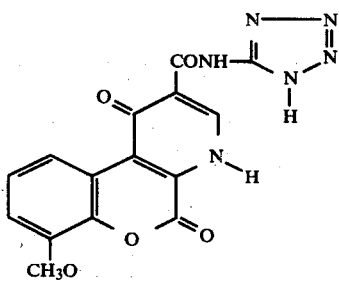

1,5-dihydro-1,5-dioxo-7-methoxy-N-1H-tetrazol-5-yl-4H-[1]benzopyrano[3,4-b]pyridine-2-carboxamide Prepared by the method described for example 17 from 1,5-dihydro-1,5-dioxo-7-methoxy-4H-1-benzopyrano[3,4-b]pyridine-2-carobxylic acid (5.82 g, 0.02 mole). Recrystallization from dimethylformamide gives pale yellow crystals (5.5 g, 78%), m.p. 315–318 (dec.).

Anal. Calcd. for $C_{15}H_{10}N_6O_5$: C, 50.85; H, 2.85; N, 23.72. Found: C, 50.79; H, 3.14; N, 23.69.

EXAMPLE 21

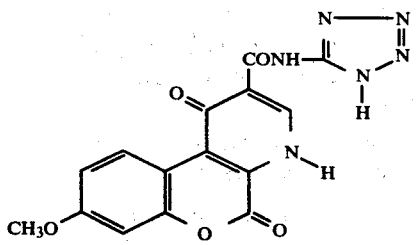

1,5-dihydro-1,5-dioxo-8-methoxy-N-1H-tetrazol-5-yl-4H-[1]benzopyrano[3,4-b]pyridine-2-carboxamide with 1H-imidazole Prepared by the general method described for example 17 from 1,5-dihydro-1,5-dioxo-8-methoxy-4H-1-benzopyrano[3,4-b]pyridine-2-carboxylic acid (2.1 g, 0.0073 mole). The product crystallized from dimethylformamide as a 1:1 salt or complex with 1H-imidazole. Recrystallization gave yellow crystals (1.61 g, 52%), m.p. 310–315 (dec.).

Anal. Calcd. for $C_{18}H_{14}N_8O_5$: C, 51.18; H, 3.34; N, 26.53. Found: C, 50.76; H, 3.71; N, 25.71.

EXAMPLE 22

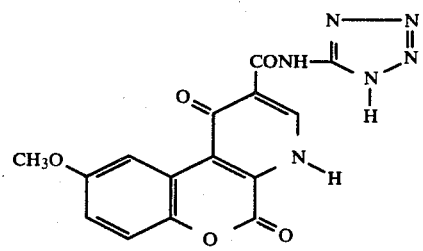

1,5-dihydro-1,5-dioxo-9-methoxy-N-1H-tetrazol-5-yl-4H-[1]benzopyrano[3,4-b]pyridine-2-carobxamide Prepared by the general method described for example 17 from 1,5-dihydro-1,5-dioxo-9-methoxy-4H-1-benzopyrano[3,4-b]pyridine-2-carboxylic acid (2.87 g, 0.01 mole). Recrystallization from dimethylformamide gives yellow crystals (2.45 g, 69%), m.p. 357–359.

Anal. Calcd. for $C_{15}H_{10}N_6O_5$: C, 50.85; H, 2.85; N, 23.72. Found: C, 51.13; H, 3.07; N, 23.58.

We claim:
1. A compound of the formula:

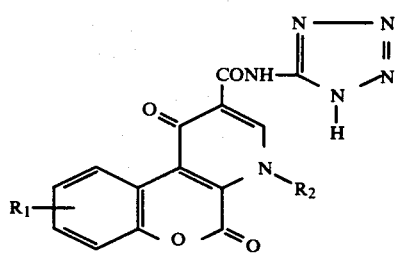

I wherein $R_1$ is hydrogen, halogen, hydroxy, lower alkoxy, lower alkyl, or nitro and $R_2$ is hydrogen or lower alkyl and the pharmaceutically acceptable salts thereof.

2. A compound of the formula which is 1,5-dihydro-1,5-dioxo-N-1H-tetrazol-5-yl-4H-[1]benzopyrano[3,4-b]-pyridine-2-carboxamide.

3. A compound according to claim 1 which is 1,5-dihydro-4-methyl-1,5-dioxo-N-1H-tetrazol-5-yl-4H-[1]benzopyrano[3,4-b]pyridine-2-carboxamide.

4. A compound according to claim 1 which is 4-Ethyl-1,5-dihydro-1,5-dioxo-N-(1H-tetrazol-5-yl)-4H-[1]benzopyrano[3,4-b]pyridine-2-carboxamide.

5. A compound according to claim 1 which is 1,5-dihydro-1,5-dioxo-7-methoxy-N-1H-tetrazol-5-yl-4H-[1]benzopyrano[3,4-b]pyridine-2-carboxamide.

6. A compound according to claim 1 which is 1,5-dihydro-1,5-dioxo-8-methoxy-N-1H-tetrazol-5-yl-[1]benzopyrano[3,4-b]pyridine-2-carboxamide with 1H-imidazole.

7. A compound according to claim 1 which is 1,5-dihydro-1,5-dioxo-9-methoxy-N-1H-tetrazol-5-yl-4H-[1]benzopyranopyrano-[3,4-b]pyridine-2-carboxamide.

* * * * *